United States Patent [19]
Gasson

[11] Patent Number: 6,083,684
[45] Date of Patent: *Jul. 4, 2000

[54] VIRAL PRODUCTS

[75] Inventor: Michael John Gasson, Dereham, United Kingdom

[73] Assignee: Agricultural & Food Research Council, Norwich, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/870,736

[22] Filed: Jun. 6, 1997

Related U.S. Application Data

[62] Division of application No. 07/877,516, Apr. 20, 1992, Pat. No. 5,763,251.

[30] Foreign Application Priority Data

Apr. 20, 1991 [GB] United Kingdom .................... 9108498

[51] Int. Cl.⁷ ........................................................ C12N 9/14
[52] U.S. Cl. .................................. 435/5; 435/18; 435/38; 435/34; 435/29
[58] Field of Search .................... 435/5, 29, 18, 435/34, 38

[56] References Cited

U.S. PATENT DOCUMENTS

| | | | |
|---|---|---|---|
| 3,002,892 | 10/1961 | Dooley | 435/5 |
| 3,094,466 | 6/1963 | Schwartz | 435/5 |
| 3,793,151 | 2/1974 | Denney | 435/5 |
| 4,618,576 | 10/1986 | Rosenstein et al. | 435/7.34 |
| 4,851,240 | 7/1989 | Day et al. | |
| 4,859,597 | 8/1989 | Yang et al. | |
| 5,006,347 | 4/1991 | Day et al. | |

FOREIGN PATENT DOCUMENTS

| | | |
|---|---|---|
| 265884 | 5/1988 | European Pat. Off. |
| WO90/00599 | 1/1990 | WIPO |

OTHER PUBLICATIONS

Jill Naylor and J. Czulak, "Host–Phage Relationship of Cheese Starter Organisms," Dairy Research Section, C.S.I.R.O., Melbourne, Australia (1956), pp. 126–131.
J.W. Pette, "The Action of Bacteriophages On Lactic Acid Bacteria," Netherlands Institute for Dairy Research, Hoorn, Netherlands, Oct. 21, 1952, pp. 1180–1184.
Nakamura et al., *Can. J. Microbiol.*, 23:601–606 (1977).
Raina, *J. Bacteriol.*, 145:661–663 (1981).
Mullan & Crawford, *J. Dairy Res.*, 52:123–138 (1985).
Garcia et al., *J. Virol.*, 61:2573–2580 (1987).
Datta et al., *Appl. Environ. Microbiol.*, 54:2933–37 (1988).
Boizet et al., *Gene*, 94:61–67 (1977).
Hirano & Imamura, *Acta Medica Univ. Kagoshima*, 14:91–101 (1972).
*Genetic Engineering News*, Feb. 1991, p. 16.
Shearman et al., *Mol. Gen. Genet.*, 218:214–221 (1989).
Egon Stark, *Microbiol. Biochemistry*, 77:215 (1972).
Romero et al., *J. of Virology*, 64:137–142 (1990).

*Primary Examiner*—Leon B. Lankford, Jr.
*Attorney, Agent, or Firm*—Dickstein Shapiro Morin & Oshinsky, LLP

[57] ABSTRACT

Bacteriophages of food-contaminating or pathogenic bacteria or the lysins thereof are used to kill such bacteria. Examples include lysins from bacteriophages of *Listeria monocytogenes* and *Clostridium tyrobutyricum*. Tests for bacterial contamination can be made specific for specific bacteria by using the appropriate bacteriophage or lysin thereof and determining whether cells are lysed thereby.

4 Claims, 13 Drawing Sheets

```
  1  AAGCTTTACT GGATAACGAC AAACTAGAAC TGACAGATGA AGGACTGAAA
 51  GGCCTTGACG AACAGCTAGG AGCATTGCAA GAAAGGCGATG CTTATTTGTT
101  TGCTCAAGAA AGCGAGGCGG GGCGGAACTG GTTTATTTGA ACAATTTACT
151  AATCGAGCTA AAAAATATGG AAAGGATGAT TAATAATGGC ATTAACAGAG
201  GCATGGCTAA TTGAAAAAGC AAATCGCAAA TTGAATACGT CAGGTATGAA
251  TAAAGCTACA TCTGATAAGA CTCGGAATGT AATTAAAAAA ATGGCAAAAG
301  AAGGGATTTA TCTTTGTGTT GCGCAAGGTT ACCGCTCAAC AGCGGAACAA
351  AATGCGCTAT ATGCACAAGG GAGAACCAAA CCTGGAGCGA TTGTTACTAA
401  TGCTAAAGGT GGGCAATCTA ATCATAATTT CGGTGTAGCA GTTGATTTGT
451  GCTTGTATAC GAGCGACGGA AAAGATGTTA TTTGGGAGTC GACAACTTCC
501  CGGTGGAAAA AGGTTGTTGC TGCTATGAAA GCGGAAGGAT TCGAATGGGG
551  CGGAGATTGG AAAAGTTTTA AAGACTATCC GCATTTTGAA CTATGTGACG
```

FIG.6A

```
601   CTGTAAGTGG TGAGAAAATC CCTACTGCGA CACAAAACAC CAATCCAAAC
651   AGACATGATG GGAAAATCGT TGACAGCGCG CCACTATTGC CAAAAATGGA
701   CTTTAAATCA AATCCAGCGC GCATGTATAA ATCAGGAACT GAGTTCTTAG
751   TATATGAACA TAATCAATAT TGGTACAAGA CGTACATCAA CGACAAATTA
801   TACTACATGT ATAAGAGCTT TTGCGATGTT GTAGCTAAAA AAGATGCAAA
851   AGGACGCATC AAAGTTCGAA TTAAAAGCGC GAAAGACTTA CGAATTCCAG
901   TTTGGAATAA CACAAAATTG AATTCTGGGA AAATTAAATG GTATGCACCC
951   AATACAAAAT TAGCATGGTA CAACAACGGA AAAGGATACT TGGAACTCTG
1001  GTATGAAAAG GATGGCTGGT ACTACACAGC GAACTACTTC TTAAAATAAA
1051  AAGTCCCGGT TTGAGCTGGG CTTTTTATTT TGAAAGTGAC TAACAAAAAA
1101  TGTAATAAAA ATGTAATAAT CCAAGTAAGT TGTATAAAAT TTGCAGAATT
1151  AGAACGTTTT ATTGATAAAT ACACCTTATG AAGAGTATTT TTGGCTATAT
1201  TTGCGCATTA TAGGGTTGAA TGTAACACTA TATGTAGAAT TC
```

```
      MetAlaLeuThrGluAlaTrpLeuIleGluLysAlaAsnArgLysLeuAsnThrSerGly
      ATGGCATTAACAGAGGCATGGCTAATTGAAGAAAAGCAAATTCGCAAATTGAATACGTCAGGT
186   ------+---------+---------+---------+---------+---------+         245
      TACCGTAATTGTCTCCGTACCGATTAACTTTTCGTTTAGCGTTTAACTTATGCAGTCCA

MetAsnLysAlaThrSerAspLysThrArgAsnValIleLysLysMetAlaLysGluGly
      ATGAATAAAGCTACATCTGATAAGACTCGGAATGTAATTAAAAAAATGGCAAAAGAAGGG
246   ------+---------+---------+---------+---------+---------+         305
      TACTTATTTCGATGTAGACTATTCTGAGCCTTACATTAATTTTTTTACCGTTTTCTTCCC

IleTyrLeuCysValAlaGlnGlyTyrArgSerThrAlaGluGlnAsnAlaLeuTyrAla
      ATTTATCTTTGTGTTGCGCAAGGTTACCGCTCAACAGCGGAACAAAATGCGCTATATGCA
306   ------+---------+---------+---------+---------+---------+         365
      TAAATAGAAACACAACGCGTTCCAATGGCGAGTTGTCGCCTTGTTTTACGCGATATACGT

GlnGlyArgThrLysProGlyAlaIleValThrAsnAlaLysGlyGlyGlnSerAsnHis
      CAAGGGAGAACCAAACCTGGAGCGATTGTTACTAATGCTAAAGGTGGGCAATCTAATCAT
366   ------+---------+---------+---------+---------+---------+         425
      GTTCCCTCTTGGTTTGGACCTCGCTAACAATGATTACGATTTCCACCCGTTAGATTAGTA

AsnPheGlyValAlaValAspLeuCysLeuTyrThrSerAspGlyLysAspValIleTrp
      AATTTCGGTGTAGCAGTTGATTTGTGCTTGTATACGAGCGACGGAAAAGATGTTATTTGG
426   ------+---------+---------+---------+---------+---------+         485
      TTAAAGCCACATCGTCAACTAAACAACGAACATATGCTCGCTGCCTTTTCTACAATAAACC

GluSerThrThrSerArgTrpLysLysValValAlaAlaMetLysAlaGluGlyPheGlu
      GAGTCGACAACTTCCCGGTGGAAAAAGGTTGTTGCTGCTATGAAAGCGGAAGGATTCGAA
486   ------+---------+---------+---------+---------+---------+         545
      CTCAGCTGTTGAAGGGCCACCTTTTTCCAACAACGACGATACTTTCGCCTTCCTAAGCTT
```

```
        TrpGlyGlyAspTrpLysSerPheLysAspTyrProHisPheGluLeuCysAspAlaVal
        TGGGGCGGAGATTGGAAAAGTTTAAAGACTATCCGCATTTGAACTATGTGACGCTGTA          605
546     ---------+---------+---------+---------+---------+---------+
        ACCCCGCCTCTAACCTTTTCAAATTTCTGATAGGCGTAAAACTTGATACACTGCGACAT

SerGlyGluLysIleProThrAlaThrGlnAsnThrAsnProAsnArgHisAspGlyLysLys
        AGTGGTGAGAAAATCCCTACTGCGACACAAAACACCAATCCAAACAGAGACATGATGGGAAA      665
606     ---------+---------+---------+---------+---------+---------+
        TCACCACTCTTTTAGGGATGACGCTGTGTTTTGTGGTTAGGTTTGTCTGTACTACCCTTT

IleValAspSerAlaProLeuLeuProLysMetAspPheLysSerAsnProAlaArgMet
        ATCGTTGACAGCGGCGCCACTATTGCCAAAAATGGACTTTAAATCAAATCCAGCGCGCATG       725
666     ---------+---------+---------+---------+---------+---------+
        TAGCAACTGTCGCCGCGGTGATAACGGTTTTTACCTGAAATTTAGTTTAGGTCGCGCGTAC

TyrLysSerGlyThrGluPheLeuValTyrGluHisAsnGlnTyrTyrTrpTyrLysThrTyr
        TATAAATCAGGAACTGAGTTCTTAGTTTATGAACATAATCAATATTGGTACAAGACGTAC       785
726     ---------+---------+---------+---------+---------+---------+
        ATATTTAGTCCTTGACTCAAGAATCATATACTTGTATTAGTTATAACCATGTTCTGCATG
```

FIG.8B

```
        IleAsnAspLysLeuTyrTyrMetTyrLysSerPheCysAspValValAlaLysLysAsp
        ATCAACGACAAATTATACTACATGTATAAGAGCTTTTGCGATGTGTAGCTAAAAAGAT         845
        ----+----+----+----+----+----+----+----+----+----+----+----+----
786     TAGTTGCTGTTTAATATGATGTACATATTCTCGAAAACGCTACACATCGATTTTTCTA

AlaLysGlyArgIleLysValArgIleLysSerAlaLysAspLeuArgIleProValTrp
        GCAAAAGGACGCATCAAAGTTCGAATTAAAAGCGCGAAAGACTTACGAATTCCAGTTTGG      905
        ----+----+----+----+----+----+----+----+----+----+----+----+----
846     CGTTTTCCTGCGTAGTTCAAGCTTAATTTTCGCGCTTTCTGAATGCTTAAGGTCAAACC

AsnAsnThrLysLeuAsnSerGlyLysIleLysTrpTyrAlaProAsnThrLysLeuAla
        AATAACACAAAATTGAATTCTGGGAAAATTAAATGGTATGCACCCAATACAAAATTAGCA      965
        ----+----+----+----+----+----+----+----+----+----+----+----+----
906     TTATTGTGTTTTAACTTAAGACCCTTTTAATTTACCATACGTGGGTTATGTTTTAATCGT

TrpTyrAsnGlyLysGlyTyrTyrLeuGluLeuTrpTyrGluLysAspGlyTyrTrpTyrTyr
        TGGTACAACGGAAAAGGATACTACTTGGAACTCTGGTATGAAAAGGATGGCTGGTACTAC     1025
        ----+----+----+----+----+----+----+----+----+----+----+----+----
966     ACCATGTTGCCTTTTCCTATGATGAACCTTGAGACCATACTTTTCCTACCGACCATGATG

ThrAlaAsnTyrPheLeuLys
        ACAGCGAACTACTTCTTAAAA       1046
        ----+----+----+----+-
1026    TGTCGCTTGATGAAGAATTTT
```

VIRAL PRODUCTS

This application is a division of application Ser. No. 07/877,516, filed Apr. 20, 1992, now U.S. Pat. No. 5,763,251.

This invention relates to the use of bacterial viruses (bacteriophages) which use bacteria as hosts and produce a bacteriophage lysin responsible for cell-wall degradation and lysis of the host cells.

Attempts to use a bacteriophage as an antimicrobial agent have failed to be effective. We have previously used the lysin of the bacteriophage φvML3 of *Lactococcus lactis* ML3, which is active against all strains of all subspecies of *Lactococcus lactis*, very weakly affects group D enterococci, but does not have any action on a wide variety of other species tested (Shearman et al (1989) *Molecular and General Genetics* 218: 214–221), to lyse cheese starter cultures (WO90/00599). WO90/00599 also discloses the use of micro-organisms, transformed to express the φvML3 lysin, to suppress populations of bacteria susceptible to the lysin, i.e. the *Lactococcus lactis* cheese starter culture strains.

It is also known to use cheese starter culture bacteria to produce the simple peptide nisin in order to destroy harmful bacteria.

We have now found that further bacteriophage lysins can be used to destroy unwanted bacteria, especially food-contaminating bacteria prejudicial to health.

A first aspect of the present invention provides a formulation comprising a lysin of a bacteriophage of a food-contaminating or pathogenic bacterium or a variant of such a lysin, substantially free of the bacteriophage.

Preferably the Listeria phage φLM4 or *Clostridium tyrobutyricum* phage φP1 lysins are used. They act against all tested species and strains of Listeria and also strains of *Kurthia zopfii*, or against *Clostridium tyrobutyricum* (as appropriate), but lack activity against other tested species.

A "variant" of such a lysin is any polypeptide of which at least 30% (preferably at least 50%, 75%, 90%, 95% or 99%) has at least 80% (preferably at least 90%, 95% or 99%) amino acid homology with the corresponding region of the lysin itself and which has at least 30% (preferably at least 50%, 75%, 90% or 95%) of the bacterial lysing capability of the said lysin.

Food-contaminating bacteria are those which, by virtue of their presence or compounds produced by them, cause undesirable flavours, odours or visual appearances or cause illness in humans or animals consuming the food.

The organism which is destroyed may be any of the following:

*Listeria monocytogenes, Clostridium tyrobutyricum, Clostridium botulinum, Clostridum perfringens*, lactic acid bacteria (eg *Lactobacillus brevis*) causing beer spoilage, Salmonella spp., Yersinia spp., Campylobacter, *E. coli*, Pseudomonas spp., Staphylococcus, Bacillus spp. (including *Bacillus cereus*), Shigella spp. and Vibrio spp.

Pathogenic bacteria include all pathogenic bacteria of humans, animals and plants. However, in a medical or veterinary context, as is explained further below, bacteria involved in topical or superficial infections are of particular interest. These include Staphylococcus spp. (eg *Staph. aureus*), Streptococcus spp., Corynebacterium spp., Clostridium spp. (eg Cl. perfringens), Yersinia spp. (eg *Y. pestis*), Pasteurella spp. (eg *P. multocida*), Streptobacillus spp. (eg *Streptobacillus moniliformis*), Proteus spp. (eg *P. mirabilis*) and Pseudonomas spp.

A second aspect of the invention provides a substantially pure preparation of a lysin from a bacteriophage of a food-contaminating or pathogenic bacterium.

A third aspect of the invention provides a coding sequence for such a lysin.

A fourth aspect provides a DNA construct comprising a coding sequence as above in an expression vehicle suitable for transformation of a microbial host or cell line.

Suitable regulatory expression vectors, transformation techniques, and hosts are all known in the art. The host may be any micro-organism or cell line which is found to express the said lysin gene, and may be a bacterium such as *E. coli* or *Lactococcus lactis*, a yeast such as *Saccharomyces cerevisiae* or *Kluveromyces lactis* or a filamentous fungus such as *Aspergillus niger*.

Thus a fifth aspect provides a microbial or cell line host transformed with such an expression vehicle and capable of expressing the lysin coding sequence.

A sixth aspect provides a polypeptide derived from the expression of the said lysin coding sequence in a suitable host transformed with such an expression vehicle.

A seventh aspect of the present invention provides a method of destroying pathogenic or food-contaminating bacteria characterised in that said bacteria are lysed with a lysin or a variant of such a lysin from a bacteriophage of such bacteria.

The use of such a preparation in food or agriculture simply involves the addition of an amount sufficient to provide an inhibitory concentration of lysin activity. The specific activity of any preparation may readily be calculated, for example by use of the spectrophotometric assay described later. The quantity of preparation necessary for effective protection in a given food may be arrived at by routine experimentation. The lysin is applied in a suitable, non-toxic aqueous medium. Any food may be treated with such a preparation by addition or application to surfaces eg of cut, cooked meat or poultry, soft cheeses and pâtés of fish or meat. The term "food" includes drinks (such as water, beer, milk and soft drinks), animal food (such as pet food or cattle food) and produce destined for consumption by humans or animals (such as stored potatoes). In agriculture, a particular application is addition to silage where Listeria and *Clostridium tyrobutyricum* are known to present a problem that can be passed on up the food chain. In brewing, brewing yeast transformed with a lysin gene may be used.

In a medical or veterinary context, because the lysin is likely to be degraded or to produce an immune reaction, it is preferred to administer it topically in diseases of the skin such as ulcers, burns and acne. It may be applied as the clinician directs, as a lotion, cream or ointment.

An eighth aspect provides a method of testing for the presence of bacteria which are lysed by a bacteriophage or by the lysin thereof, comprising exposing a sample to the said bacteriophage or lysin and determining whether bacteria have been lysed as a result of such exposure.

Any technology that exploits the release of intracellular biochemicals (eg ATP or enzymes such as alkaline phosphatase or esterase) to detect micro-organisms can, in accordance with the invention, be made specific for the target range of such lysins. For example, an ATP or phosphatase release test for Listeria using the Listeria bacteriophage or lysin thereof, in which the release of ATP or phosphatase is detected (eg by linkage to a luciferase reaction and monitoring of photon release or by spectrophotometric methods as is described below) indicates the specific presence of Listeria in a sample. The invention further provides a kit comprising a lysin and means to detect bacterial lysis.

Preferably, the bacteriophage in all these contexts is or at least includes *Listeria monocytogenes* φLM4 or a bacteriophage of *Clostridium tyrobutyricum*, such as φP1. Several different lysins may be used in order to destroy or identify a specific range of bacteria.

The cloning and characterization of the gene for the lysin of the Listeria bacteriophage φLM4 has facilitated the production of the free lysin and the availability of its structural gene. These components have application in the protection of environment and food material from pathogenic strains of Listeria. The free lysin acts as a novel antimicrobial that kills such bacteria and the gene can be genetically engineered in a non-pathogenic micro-organism such that the latter produce the Listeria lysin thereby equipping it with a novel anti-Listeria capability. For example, a food-grade micro-organism may be transformed with a DNA construct comprising a coding sequence for the lysin.

Preferred embodiments of the invention will now be described by way of example with reference to the accompanying drawings, in which:

FIG. 2 is a restriction and deletion map of lysin-expressing clone pFI322. The result of lysin activity tests is indicated to the right. The inferred location of the lysin gene is shown. Arrows indicate the orientation of the lysin gene with respect to the lac α promoter of the pUC vector used which is transcribed from left to right in this figure (i.e. pFI324 is opposed to the lac α promoter, other clones are transcribed in the same direction as the lac α promoter).

Plasmid pF1322 is pUC18 carrying a 3.6 kb HindIII fragment of bacteriophage φLM4 DNA. Plasmid pF1326 is pFI322 with a 0.56 kb HindIII—SalI deletion. Plasmid pFI327 is pFI322 with a 1.32 kb HindIII—EcoRI deletion. Plasmid pFI324 is pUC18 carrying a 1.9 kb HindIII—NruI fragment of pFI322 cloned between its HindIII and HincII sites. Plasmid pFI325 is pUC18 carrying a 1.6 kb NruI—HindIII fragment of pFI322 cloned between its HincII and HindIIII sites. Plasmid pFI328 is pUC19 carrying a 1.9 kb HindIII—NruI fragment of pFI322 cloned between its HindIII and HincII sites. Plasmid pFI329 is pFI328 carrying a 1.6 kb BaβI deletion from the polylinker BamHI site. Plasmid pFl330 is pFI328 carrying a 1.6 kb BaβI deletion from the polylinker BamHI site.

FIG. 5 illustrates the sequencing strategy used. The extent and direction of sequences determined are indicated by the arrows. Synthetic oligonucleotide primers are indicated by boxes.

EXAMPLE 1

CLONING OF LYSIN GENE, ETC

Isolation of Bacteriophage φLM4

A bacteriophage named φLM4 was isolated from a culture of *Listeria monocytogenes* serotype 4b that was originally obtained from a listeriosis outbreak in Nova Scotia, Canada in 1981. The source of the infection was tracked down to contaminated coleslaw. This culture of *Listeria monocytogenes* was deposited under the Budapest Treaty as NCTC 12452 in the National Collection of Type Cultures, Central Public Health Laboratory, Colindale, London, UK on Mar. 21, 1991. The bacteriophage was purified by standard single plaque isolation procedure using *Listeria monocytoqenes* F6868 as the host. This culture was similarly deposited under the Budapest Treaty as NCTC 12453 in the National Collection of Type Cultures, Central Public Health Laboratory, Colindale, London, UK on Mar. 21, 1991. Examination of this bacteriophage by electron microscopy revealed it to have an isometric head with a diameter of approximately 50 nm and a tail of approximately 250 nm.

Isolation of DNA from *Listeria monocytogenes* Bacteriophage φLM4

20 ml of an 18 hour culture of *Listeria monocytogenes* F6868 was inoculated into 500 ml of Bacto tryptose phosphate broth and incubated with shaking at 30° C. When O.D. 600 reached 0.15 the culture was infected with $5 \times 10^{10}$ p.f.u. of bacteriophage φLM4 and incubated until lysis was apparent as a loss of turbidity. The lysate was centrifuged at 6000 xg for 10 min at 4° C. The bacteriophage lysate was then concentrated by polyethylene glycol precipitation and purified on caesium chloride stepped gradients using well established protocols (Bachrach and Friedmann (1971) *Applied Microbiology* 22: 706–715). Bacteriophage DNA was extracted by dialysis against 50% formamide in TE buffer (0.1 Tris—HCl, 0.01M EDTA, pH 8.5). Further purification was then performed on caesium chloride-ethidium bromide equilibrium density gradients. Examination of the bacteriophage DNA by agarose gel electrophoresis revealed the genome to be approximately 39 kb in size.

Cloning the Bacteriophage φLM4 Lysin Gene

DNA purified from bacteriophage φLM4 was digested with restriction endonuclease HindIII and ligated to plasmid pUC18 vector DNA that had also been cleaved with restriction endonuclease HindIII. The ligated DNA was transformed into *Escherichia coli* TB1 and ampicillin resistant colonies were selected on LB agar containing 50 μg/ml ampicillin, 40 μg/ml isopropyl-β-D-thiogalactopyranoside (IPTG) and 40 μg/ml 5-bromo-4-chloro-3-indolyl-β-D-galactopyranoside (X-gal). These steps were performed using well established protocols (Sambrook, J. et al (1989), Molecular Cloning. A laboratory manual. Cold Spring Harbor Laboratory, Cold Spring Harbor, N.Y., 2nd Edition).

Figure 1:
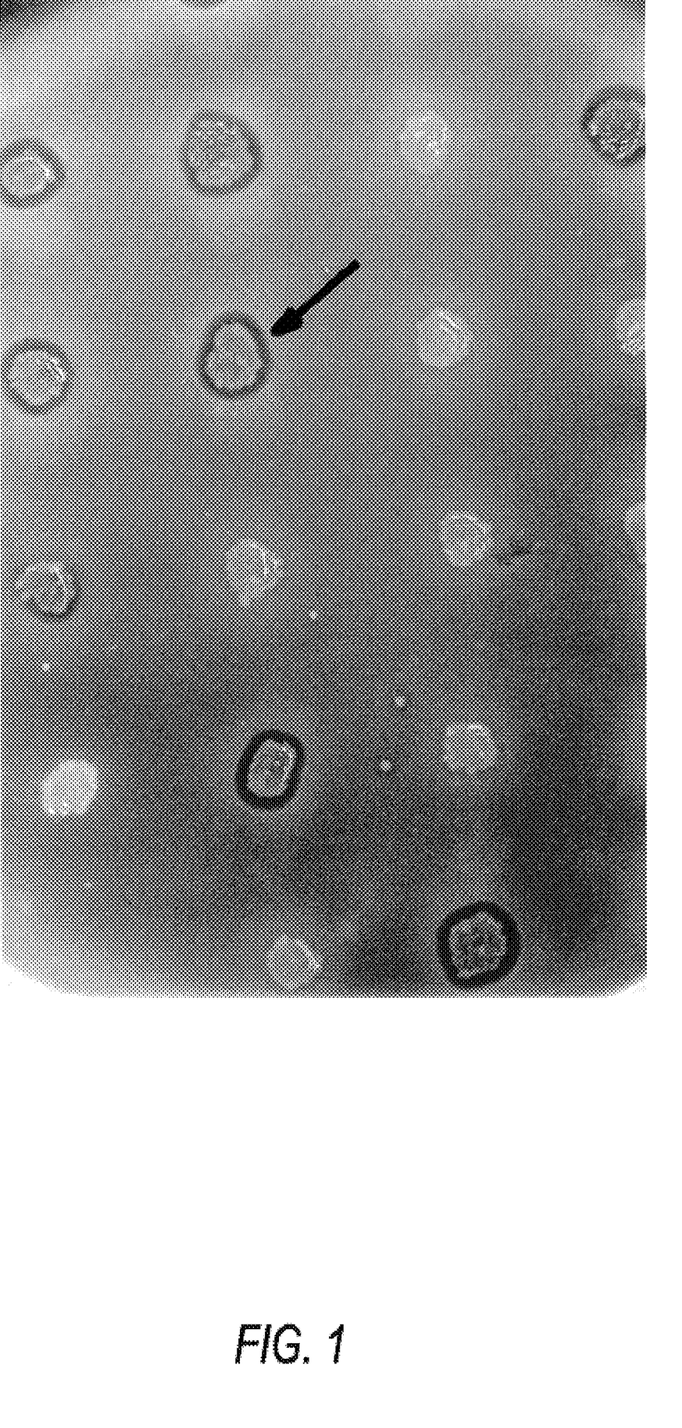
FIG. 1 shows patches of *E. coli* clones with HindIII fragments of φLM4 DNA in the HindIII site of vector pUC18. The plate is overlayed with a suspension of *Listeria monocytogenes* 6868 cells and lysin producing clones create clear zones around the patch (indicated by an arrow).

White colonies were screened for their ability to produce a bacteriophage lysin active against *Listeria monocytogenes*. These colonies were patched onto duplicate Bacto tryptose agar plates and incubated for 18 hours at 37° C. One plate was exposed to chloroform vapour for 10 min and then seeded with 0.2 ml of an 18 hour broth culture of *Listeria* monocytogenes F6868. After incubation at 30° C. for 18 hours clear zones of lysins were apparent around patches of clones expressing the Listeria bacteriophage φLM4 lysin. This is illustrated in FIG. 1. Positive clones were recovered from the duplicate plate and the pUC18 derivative plasmid isolated and characterized by digestion with restriction endonuclease HindIII. One lysin expressing pUC18 clone that contained a 3.6 kb insert of φLM4 DNA was chosen for further analysis. This plasmid was designated pFI322.

Deletion Analysis of Lysin Expressing Plasmid pF1322

Characterization of pFI322 was undertaken by constructing a restriction map of this insert using single and double digests with a variety of restriction enzymes. The map is presented in FIG. 2. Deletion of some regions of the 3.6 kb insert contained in pPI322 was achieved by digestion with certain of these enzymes, religation and transformation into E. coli TB1. In other instances endonuclease Bal 31 was used to introduce deletions. In addition, some regions of the 3.6 kb cloned DNA in pFI322 were deleted by digestion with certain restriction endonucleases and re-cloning into appropriately cleaved plasmid vectors pUC18 or pUC19 and transformation into E. coli TB1. These manipulations are clearly documented in FIG. 2 which is presented in the form of a deletion map for pFI322. After confirming that the various constructed plasmids derived from pFI322 had the expected structures, these clones were tested for their ability to produce Listeria bacteriophage lysin. As well as the plate assay described above and illustrated in FIG. 1, a spectrophotometric assay was also used. For this the E. coli strain carrying plasmid clones were grown at 37° C. for 18 hours, harvested by centrifugation at 6000 xg for 5 min at 4° C., washed down once in 100 mM Tris buffer pH7.5 and resuspended in this same buffer at approximately 10 mg dry weight/ml. Cell free extracts were made by 6 cycles of ultrasonication (15 sec on, 10 sec off) at 0° C. using the microprobe of an MSE Soniprep 150. Unbroken cells and cell debris were removed by centrifugation at 25000 xg for 15 min at 4° C.

Samples of the cell free extracts were added to an equilibrated (5 min at 37° C.) 4 ml reaction mixture containing 400 μmole Tris HCl pH7.5 and Listeria monocytogenes F6868 indicator cells that had been harvested and resuspended at an O.D. 600 of 2.3. The fall in optical density caused by lysis of indicator cells was followed using a spectrophotometer. Typical results from use of this protocol are presented in FIG. 3. The lytic activity of the plasmid derivative described above and in FIG. 2 were assessed using both of these methods and the results are presented in FIG. 2.

Figure 2:
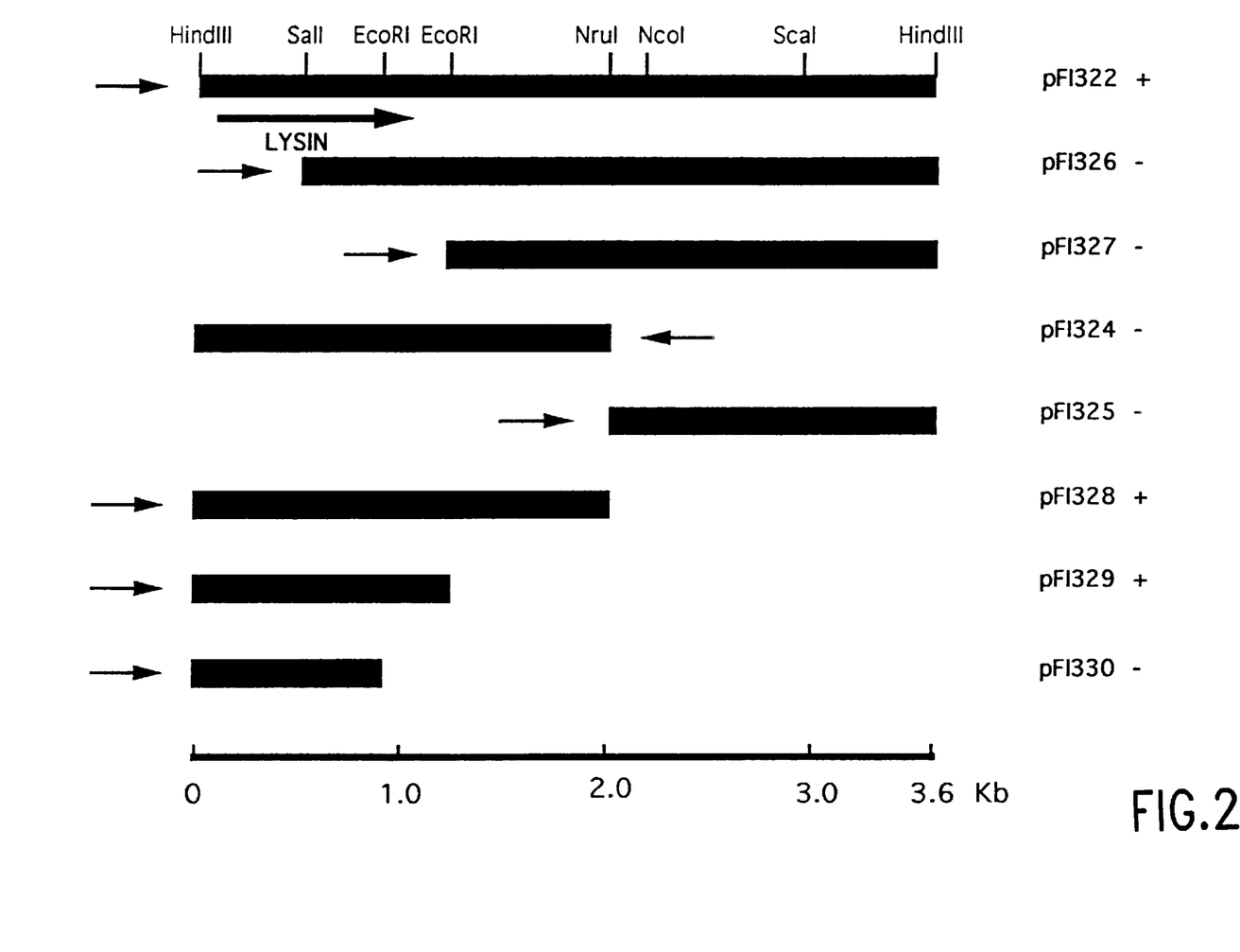

These results demonstrated that the structural gene for bacteriophage φLM4 was contained within the left hand 1.2 kb of the DNA cloned in pFI322 and defined by the HindIII site at co-ordinate 0 and the EcoR1 site at co-ordinate 1.25 of the map illustrated in FIG. 2.

FIG. 2 also indicates the orientation of Listeria bacteriophage φLM4 DNA with respect to the E. coli lac α promoter that is present on vectors pUC18 and pUC19. It is apparent that a positive reaction in the lysin assay is only found when one orientation is maintained (eg pFI324 is negative whereas pFI328 is positive even though both constructs contain the same Listeria bacteriophage φLM4 fragment). This suggests that expression of the lysin gene depends on use of the E. coli lac α promoter and that no Listeria bacteriophage φLM4 promoter is present and active in E. coli.

Detection of the Lysin Protein

In order to identify a protein produced by the fragment of φLM4 DNA that expressed lysin activity another E. coli vector was used. A 2 kb fragment from plasmid pFI328 between the HindIII site at co-ordinate 0 and a unique BamHI site present on the polylinker of pUC19 was isolated and cloned between the HindIII and BamHI sites of the T7 expression vector pSP73 that was purchased from Promega. The constructed plasmid named pFI331 was transformed into the E. coli host strain JM109DE3.

The E. coli T7 promoter in this vector is expressed by the phage specific T7 RNA polymerase which is induced by addition of IPTG in the appropriate host strain E. coli JM109 DE3. Cultures of this strain carrying pSP73 as a control or pFI331 were grown for 3 hours and induced by addition of 1PTG to a final concentration of 0.2 mM. Incubation was continued for a further 3 hours before the cultures were harvested and used to prepare cell extracts using well-established, published procedures (Studier, F. W., Rosenberg, A. H., Dunn, J. J. and Dubendorff, J. W. (1990) Methods in Enzymology 185: 60–89).

Figure 4:
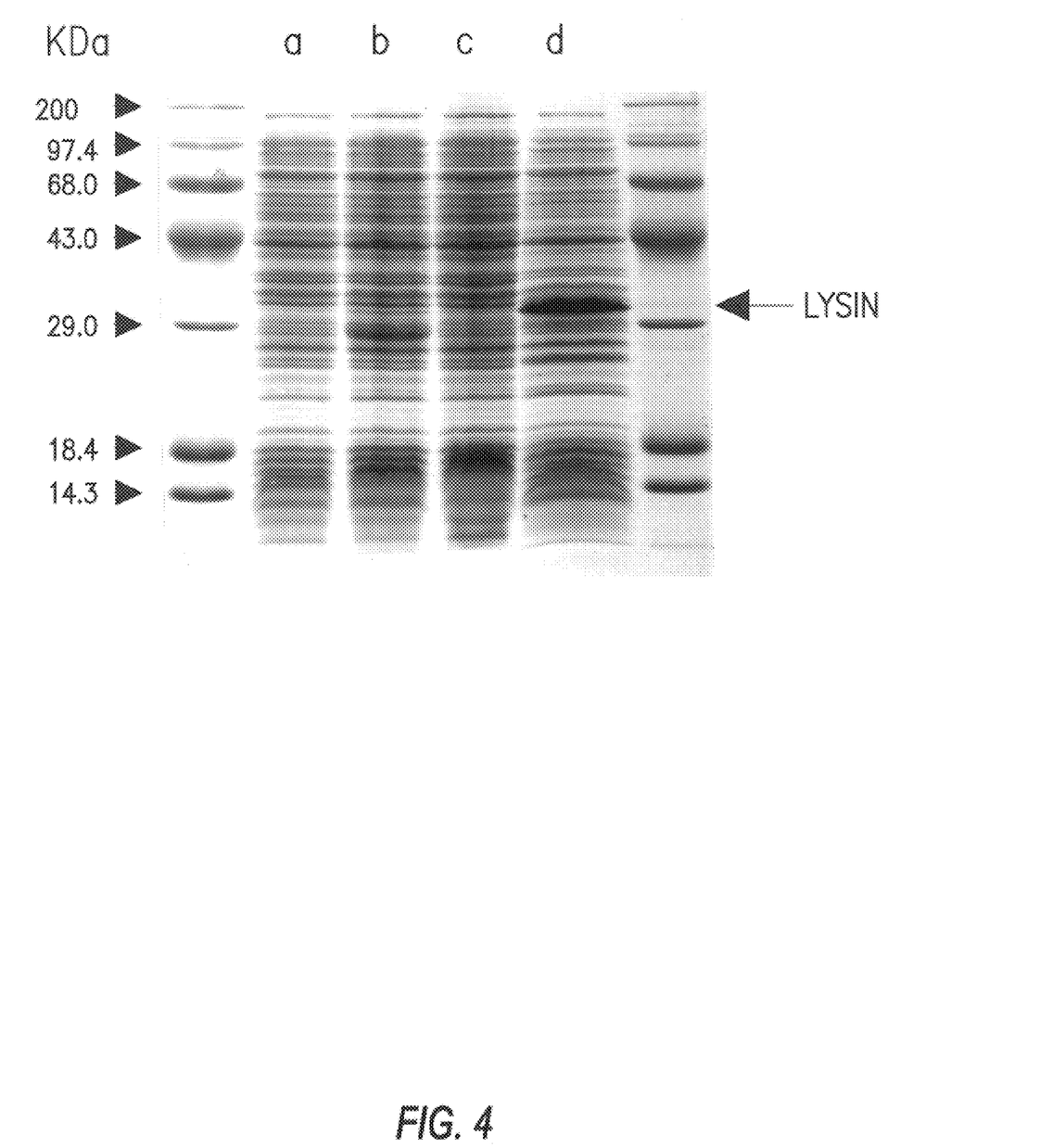
FIG. 4 is a Coomassie blue stained SDS polyacrylamide gel of proteins produced by *E. coli* strain carrying the T7 expression vector pSP73 (tracks 2 and 3) or pFI331 which carries the lysin gene (tracks 4 and 5). Uninduced cells (tracks 2 and 4) are compared with induced cells (tracks 3 and 5). Molecular weight markers are present (tracks 1 and 6) and the expressed lysin protein is indicated by an arrow.

Proteins present in cell extracts were analysed using conventional SDS-polyacrylamide gel electrophoresis (Laemmli (1970) Nature 227: 680–685). The results presented in FIG. 4 clearly demonstrate that the 2 kb fragment of pFI331 expresses a single protein with a molecular size of 31 kilodaltons which represents the lysin enzyme.

DNA Sequence of the Listeria Bacteriophage φLM4 Lysin Gene

Figure 5:
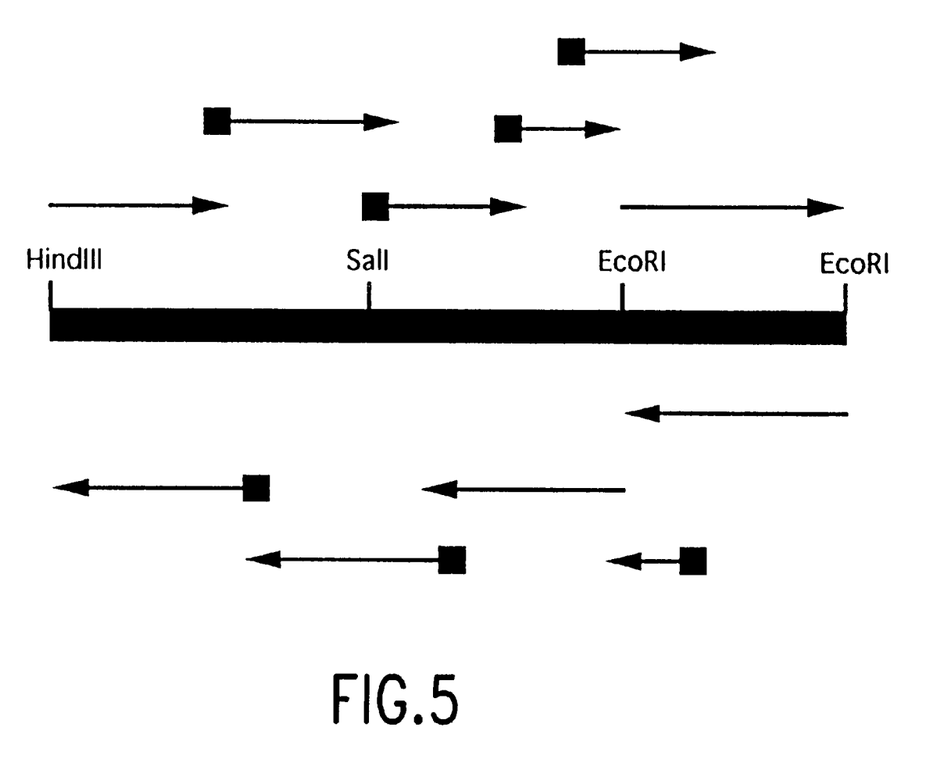
Figure 6A:
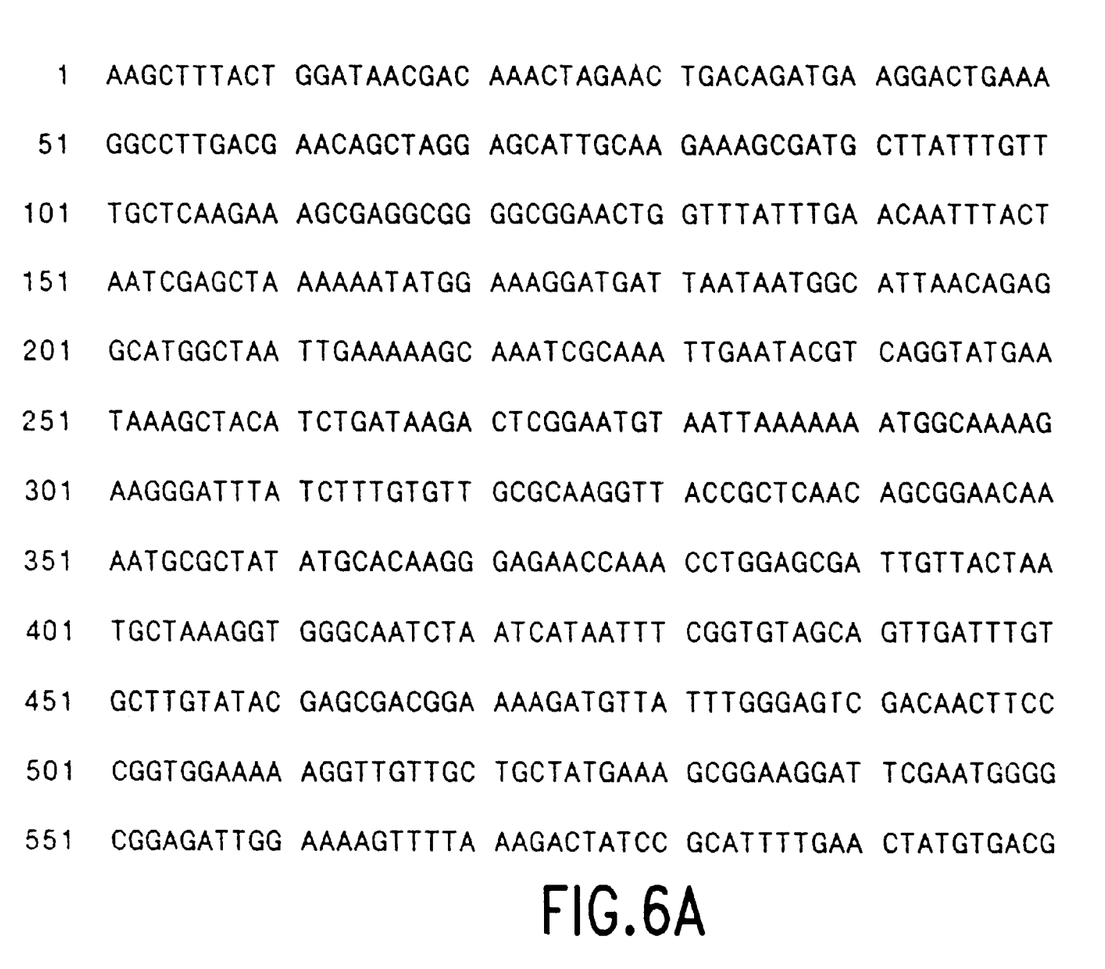
FIG. 6 shows a single strand of the region of φLM4 DNA that encodes the lysin gene.
Figure 6B:
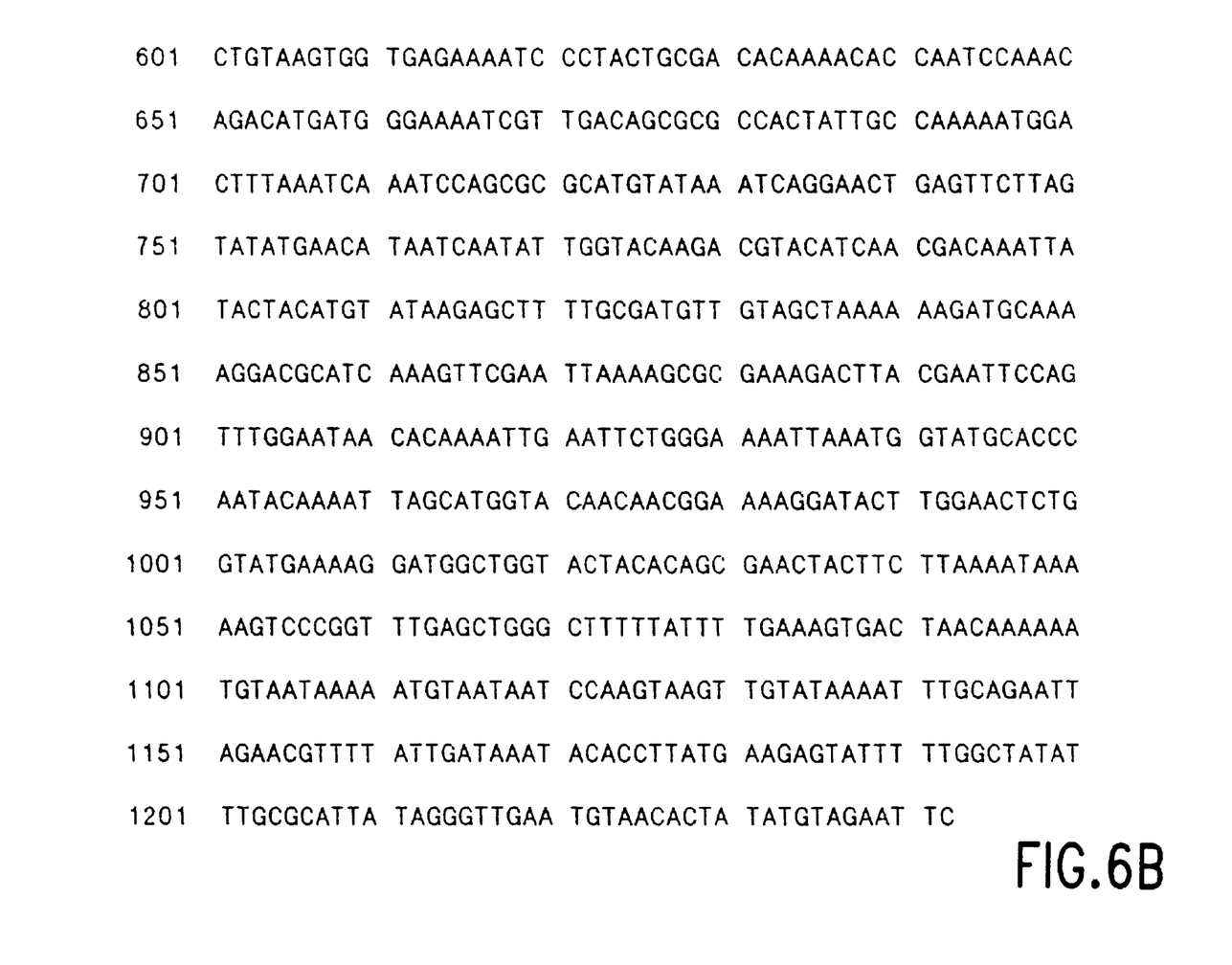
Figure 7A:
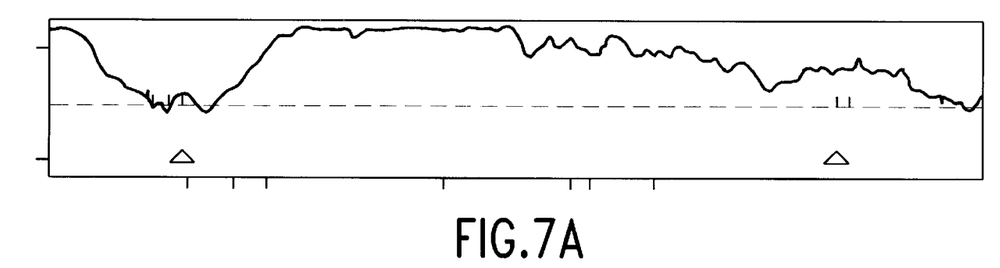
FIG. 7 is the Analyseq print out of the analysis of the DNA sequence shown in FIG. 6. The identification of the open reading frame of the lysin gene is in the top panel.
Figure 7B:
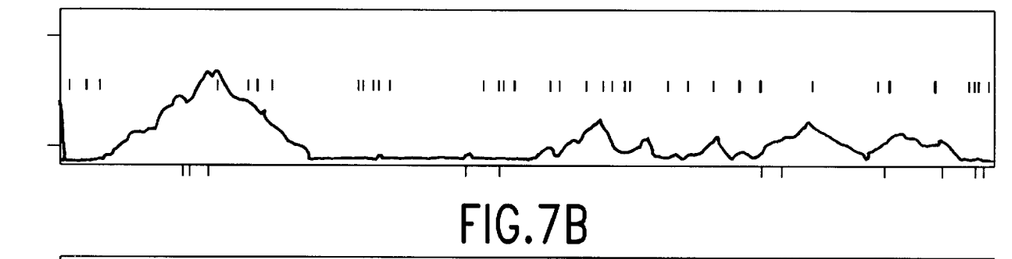
Figure 7C:
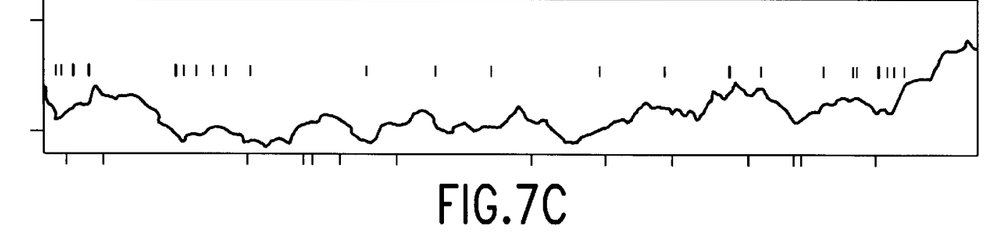
Figure 7D:
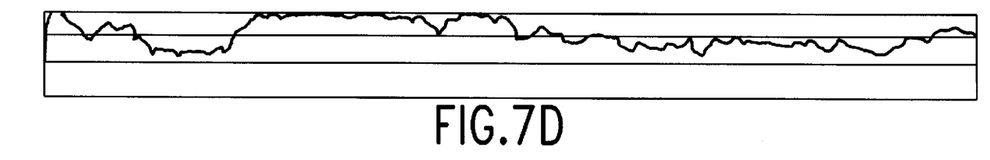
Figure 8A:
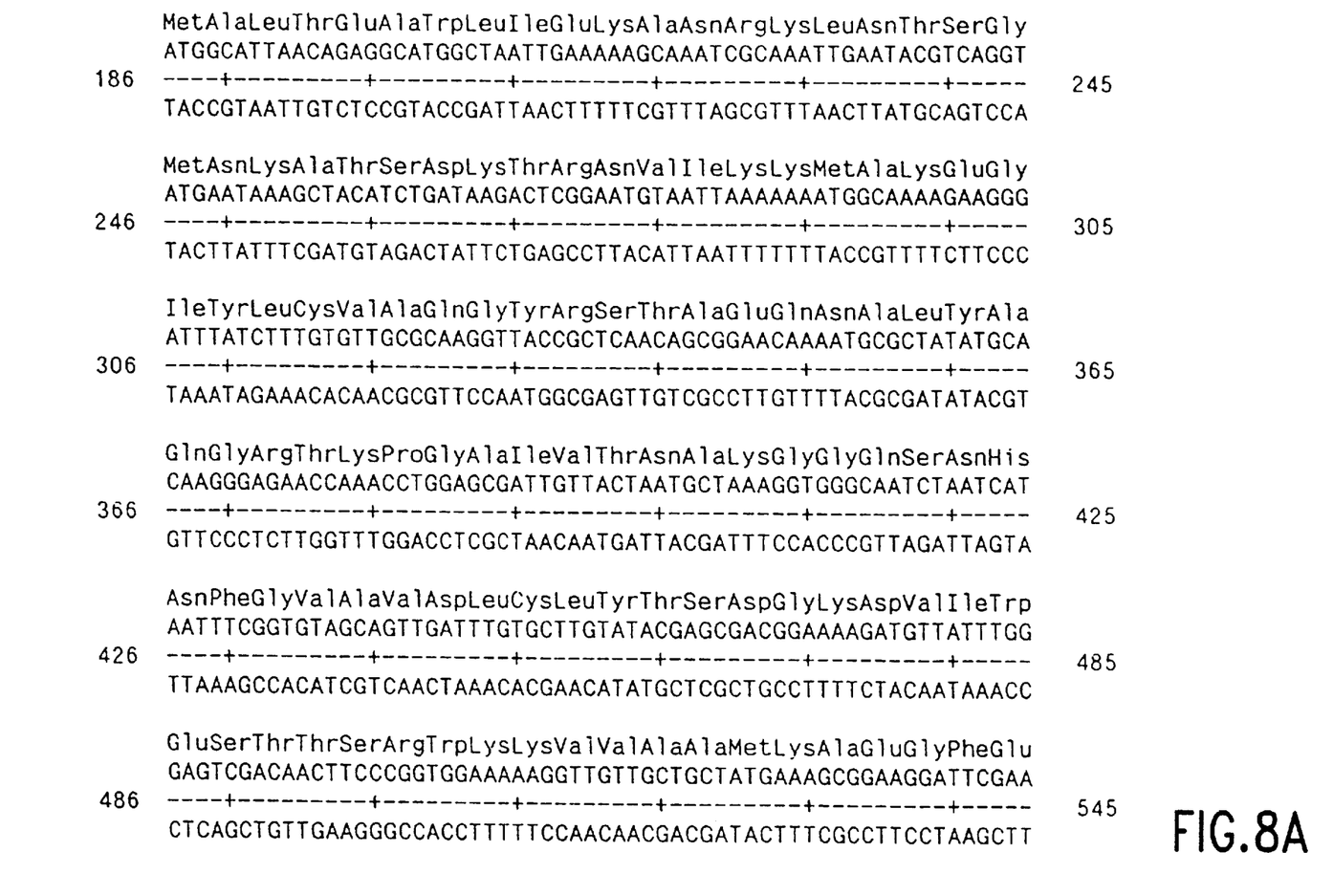
FIG. 8 shows the double stranded DNA sequence of the lysin structural gene and its translated protein product.
Figure 8B:
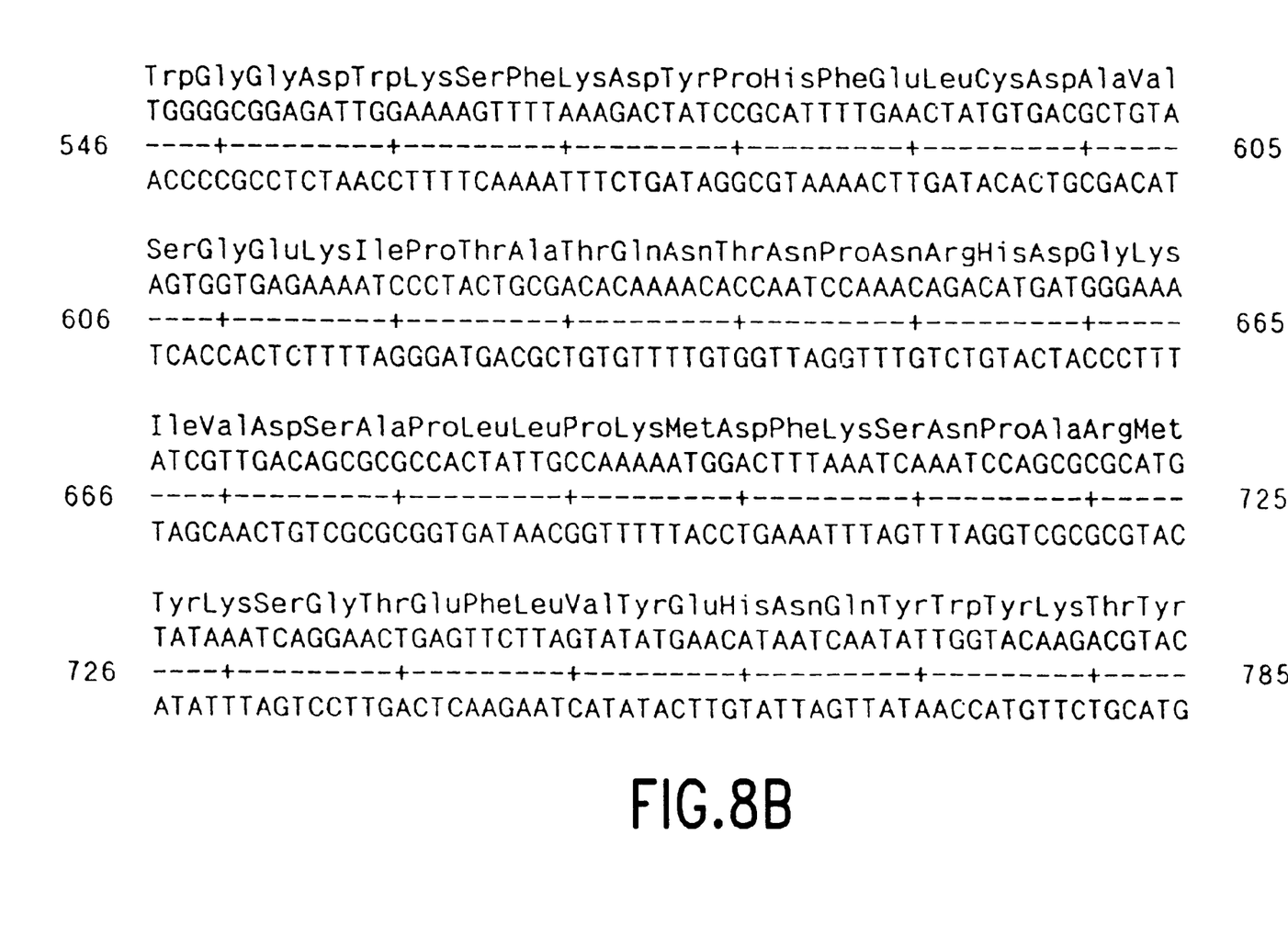
Figure 8C:
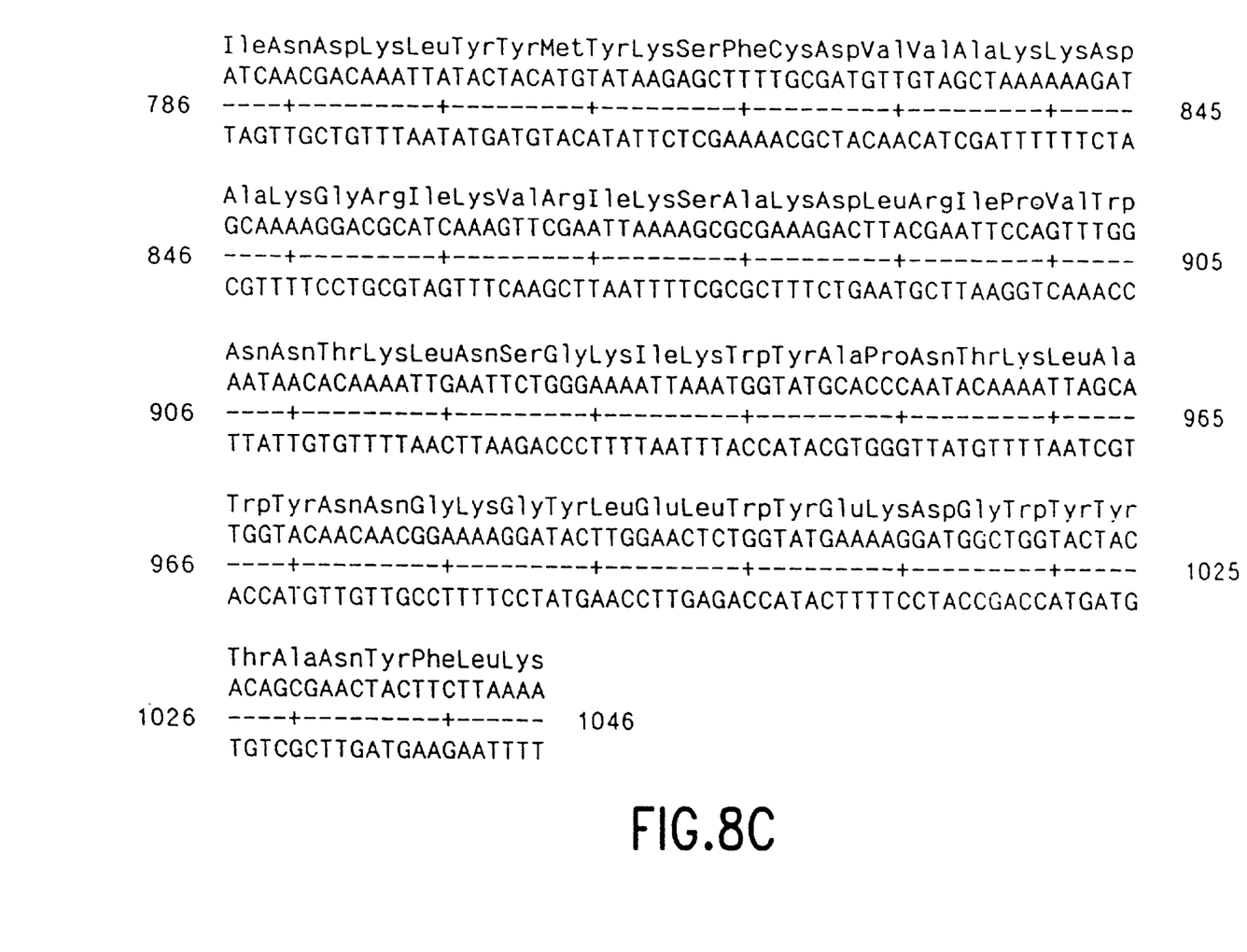

The region of DNA between co-ordinate 0 and 1.2 in FIG. 2 was subject to oligonucleotide sequence analysis using the dideoxy chain-termination method (Sanger, F., Coulson, A. R., Barrell, B. G., Smith, A. J. H. and Roe, B. A. (1980) J. Molec. Biol. 143) with a sequenase version 2.0 kit (United States Biochemical Corporation). The 0.9 kb HindIII—EcoRI and the 0.3 kb EcoRI—EcoRI fragments of pFI328 were subcloned in the M13 sequencing vectors M13mp18 and M13mp19 to create templates and sequenced using universal and synthetic oligonucleotide primers. To sequence across the internal EcoRI site at co-ordinate 0.9 double stranded sequencing of pFI329 plasmid DNA was used. The sequencing strategy is presented in FIG. 5 and the complete DNA sequence is in FIG. 6. The sequence was analysed using the computer programme ANALYSEQ (Staden (1980) Nucleic Acid Research 8: 3673–3694) which revealed an open reading frame that represents the Listeria bacteriophage lysin gene. The printout from the Analyseq analysis is presented in FIG. 7 and the open reading frame representing the lysin structural gene and its translated protein product is presented in FIG. 8. The molecular size of the translated protein was calculated to be 32.9 kilodaltons which agrees well with the calculated 31 kilodalton size of the protein expressed by the T7 vector pSP73 (Clone pFI331 in FIG. 4).

Activity and Specificity of the Listeria Bacteriophage φLM4 Lysin

Figure 3:
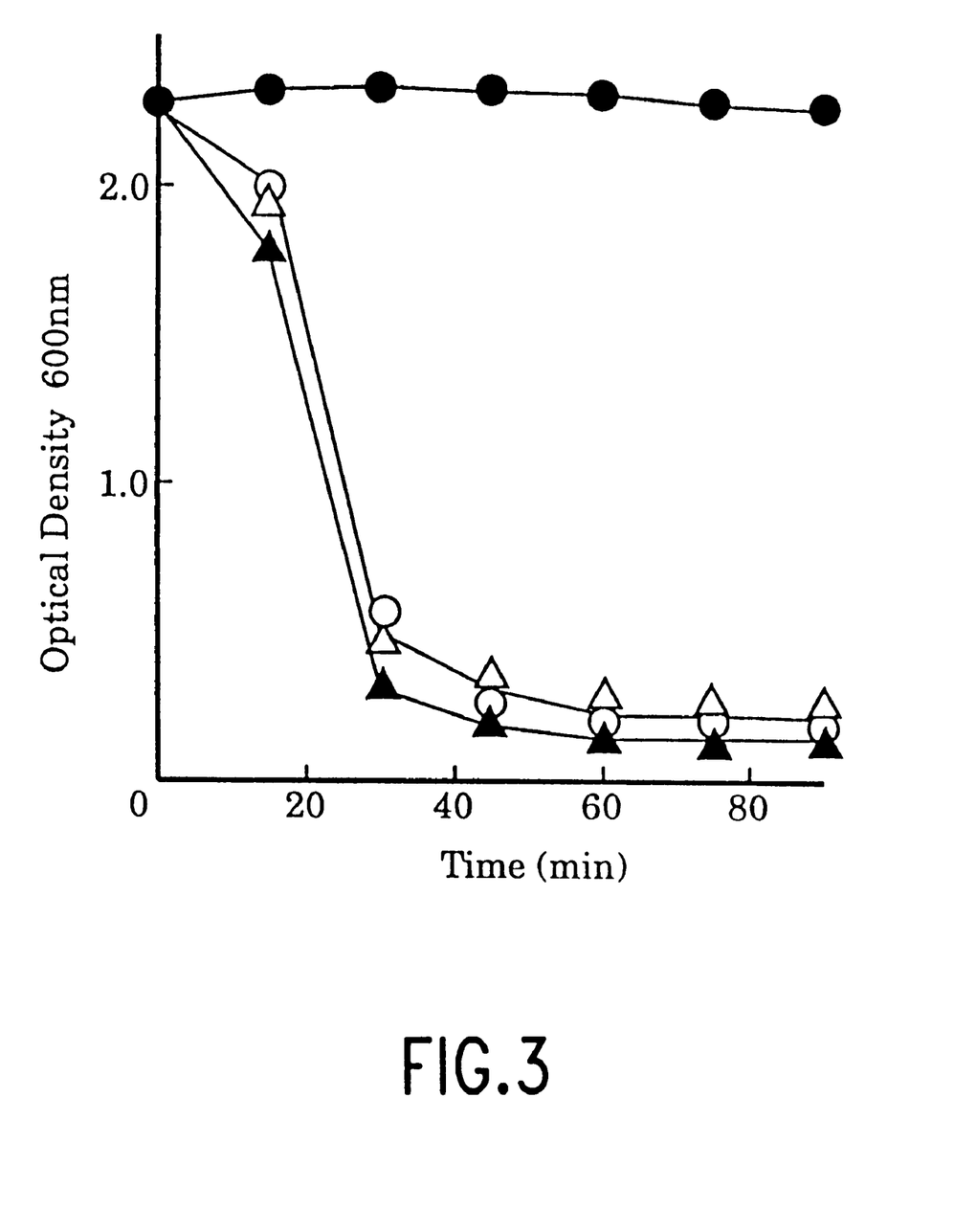
FIG. 3 illustrates the response of a suspension of *Listeria monocytogenes* 6868 cells to cell free extracts of *E. coli* strains harbouring plasmids pFI322(▲), pFI328(Δ), pFI329 (○) and pUC19(●).

FIG. 3 illustrates the lytic activity of crude cell free extracts of E. coli TB1 carrying the plasmids pFI322, pFI328, pFI329 and pUC19 assayed using the spectrophotometric method described above. This activity was related to units of commercially available mutanolysin (Sigma) as has been described previously (Shearman, C., Underwood, H, Jury, K. and Gasson M. (1989) Mol. Gen. Genetics 218: 214–221). The crude cell extracts of lysin expressing clones typically contained 5000 mutanolysin equivalent units per mg. protein.

In order to test the spectrum of activity of this lysin, the spectrophotometric assay was performed on 16 serotypes of Listeria monocytogenes, all other species of Listeria, the related species Kurthia zopfii and a variety of other gram positive and gram negative bacteria. The results compiled in Table 1 show that the Listeria bacteriophage φLM4 lysin was active against all tested strains of *Listeria monocytogenes, Listeria innocua, Listeria ivanovii, Listeria murrayi, Listeria seelegri, Listeria welshimeri, Listeria grayi* and *Kurthia zopfii*. No activity was found against any of the other species tested.

TABLE 1

ACTIVITY OF CLONED LYSIN AGAINST LISTERIA SPECIES

| Organism | Strain | Serotype | Relative[a] Activity | Time (min)[b] ΔOD$_{600}$ = 1 |
|---|---|---|---|---|
| *Listeria monocytogenes* | F6868 | 4b | 1.00 | 20 |
| | NCTC 7973 | 1a | 0.19 | 53 |
| | NCTC 5412 | 4b | 0.90 | 13 |
| | F4642 | 4b | 0.92 | 14 |
| | NCTC10357 | 1a | 0.92 | 20 |
| | BL87/41 | 4 | 0.66 | 25 |
| | NCTC 5348 | 2 | 0.10 | 78 |
| | SLCC2373 | 3a | 1.20 | 17 |
| | SLCC2540 | 3b | 0.19 | 60 |
| | SLCC2479 | 3c | 0.15 | 60 |
| | SLCC2374 | 4a | 0.54 | 30 |
| | SLCC2376 | 4c | 0.19 | 90 |
| | SLCC2377 | 4d | 0.08 | 90 |
| | SLCC2378 | 4e | 0.56 | 28 |
| | SLCC2482 | 7 | 0.45 | 36 |
| | L3056 | 1/2a | 0.49 | 30 |
| | L4203 | 1/2a | 0.36 | 41 |
| | L4490 | 1/2b | 0.29 | 55 |
| | L1378 | 1/2b | 0.09 | 150 |
| | L4281 | 1/2c | 0.11 | 120 |
| | L3304 | 1/2c | 0.12 | 90 |
| | L3253 | 4bx | 0.66 | 26 |
| | L2248 | 4bx | 0.08 | 72 |
| *Listeria innocua* | NCTC11288 | 6a | 0.90 | 12 |
| | NCTC11289 | 6a | 0.69 | 22 |
| *Listeria ivanovii* | NCTC11007 | | 0.95 | 18 |
| | SLCC5579 | | 0.51 | 30 |
| *Listeria seeligeri* | NCTC11856 | | 1.10 | 15 |
| *Listeria welshimeri* | NCTC11857 | | 0.29 | 36 |
| *Listeria murrayi* | NCTC10812 | | 0.86 | 15 |
| *Listeria grayi* | NCTC10815 | | 0.93 | 12 |
| *Kurthia zopfii* | NCTC10597 | | 0.54 | 28 |

Table 1 shows the relative sensitivity of a selection of strains of Listeria and *Kurthia zopfii* to the bacteriophage φLM4 lysin. a) Relative activity is the fall in optical density (O.D$_{600}$) from 2.3 achieved in 30 minutes divided by the equivalent fall obtained using *Listeria monocytogenes* F6868. b) The time (min) taken for a fall in optical density of O.D.$_{600}$ from 2.3 to 1.3 (O.D.$_{600}$ fall of 1) is recorded. Other strains tested which show no sensitivity to lysin were *Aeromonas hydrophila* NCTC 8049, *Bacillus cereus* NCTC 11143, *Brocothrix thermosphacta* NCTC 10822, *Carnobacterium pisciola* BL90/14, *Enterococcus faecalis* BL90/11, *Escherichia coli* BL90/12, *Klebsiella pneumoniae* NCFB 711, *Pseudomonas fluorescens* BL 78/45, *Staphylococcus aureus* NCTC 10652, *Streptococcus pneumoniae* NCTC 7465, *Streptococcus pyogenes* NCTC 2381.

In addition it was observed that the lysin was active at temperatures as low as 2° C. At 2° C. addition of lysin to suspensions of *Listeria monocytogenes* caused a decrease of between 0.7 and 2.0 O.D.$_{600}$ units within 24 hours.

EXAMPLE 2

USE OF LYSIN TO CONTROL LISTERIA

Use as a Free Lysin

There are two distinct application concepts. One exploits a preparation of lysin enzyme manufactured by fermentation of a genetically engineered micro-organism that expresses the lysin gene product (Free lysin). The host organism may be *E. coli*, or any other bacterial species such as *Lactococcus lactis*, a yeast such as *Saccharomyces cerevisiae* or *Kluveromyces lactis* or a filamentous fungus such as *Aspergillus niger*. The lysin gene may be expressed intracellularly in which case a preparation may consist of a cell free lysate of the producing organism with some purification of the lysin, for example by ammonium sulphate precipitation and/or column chromatography. Alternatively the fermentation micro-organism may secrete lysin into the culture medium in which case the supernatant of the centrifuged fermentation broth provides the basis of a preparation, which again may require some purification.

Figure 9:
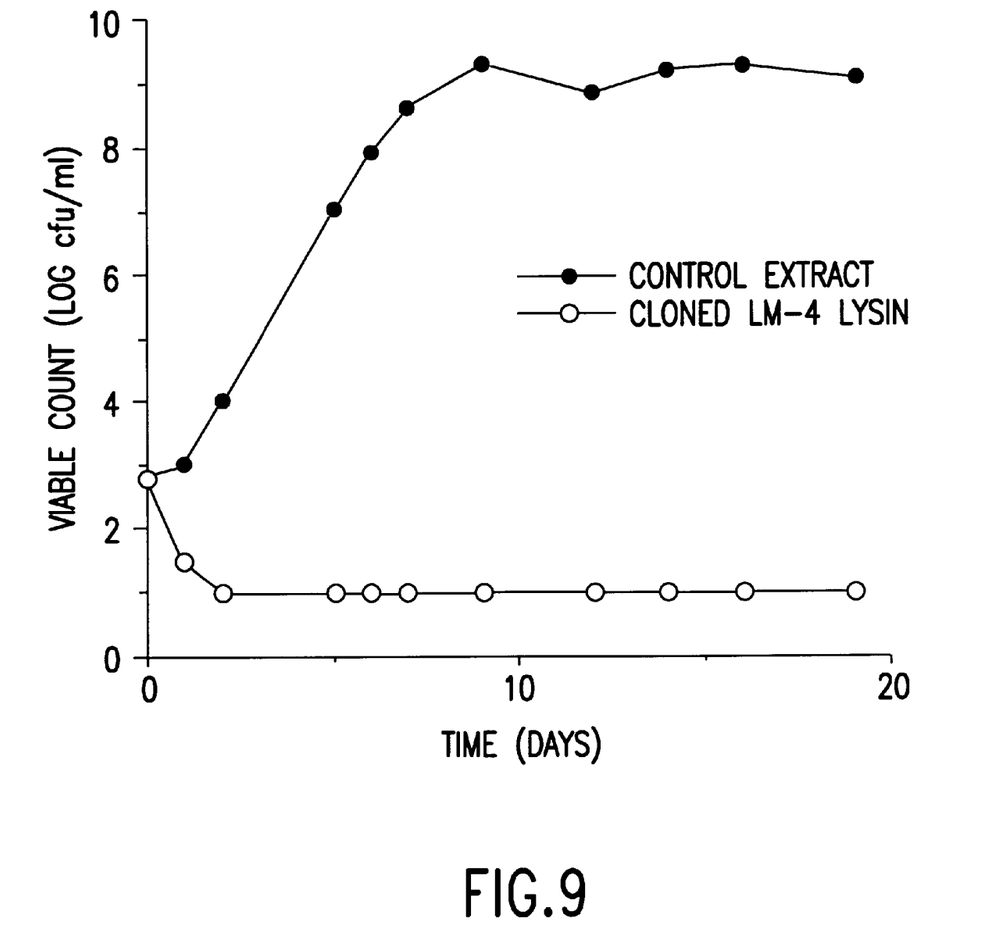
FIG. 9 shows the protective effect of cloned Listeria lysin on skimmed milk to which *Listeria Monocytogenes* is added.

The effectiveness of a crude extract of cloned Listeria lysin was demonstrated by its addition to skimmed milk containing *Listeria monocytogenes*. As illustrated in FIG. 9 the lysin preparation reduces the viable count of *Listeria monocytogenes* and after 22 days incubation at 8° C. there is a viable count difference of 10$_8$ *Listeria cfu* between milk containing lysin and the control sample.

Expression of Lysin by a Genetically Engineered Micro-organism

An alternative application concept is to use a genetically engineered micro-organism that is compatible with a food or agricultural environment such as a species of lactic acid bacteria. Such an organism then grows in a food or agricultural environment and expresses an introduced gene for Listeria bacteriophage lysin. The gene may be expressed intracellularly and released into food or an agricultural environment by autolysis or induced lysis of that micro-organism. Alternatively the lysin may be secreted by a micro-organism so that active lysin is released into a food or agricultural environment by that viable micro-organism. In these cases the lysin gene is placed downstream of an appropriate promoter such as the lactose operon promoter or the proteinase promoter of *Lactococcus lactis* NCFB 712. Secretion may be achieved by fusion of the lysin structural gene to a known N terminal secretory leader such as those of the proteinase gene, the usp45 gene or the nisin precursor gene of *Lactococcus lactis*. Suitable organisms for this application concept include strains of *Lactococcus lactis* in cheese and dairy products and *Lactobacillus plantarum* or Pediococcus species in agricultural silage.

Figure 10:
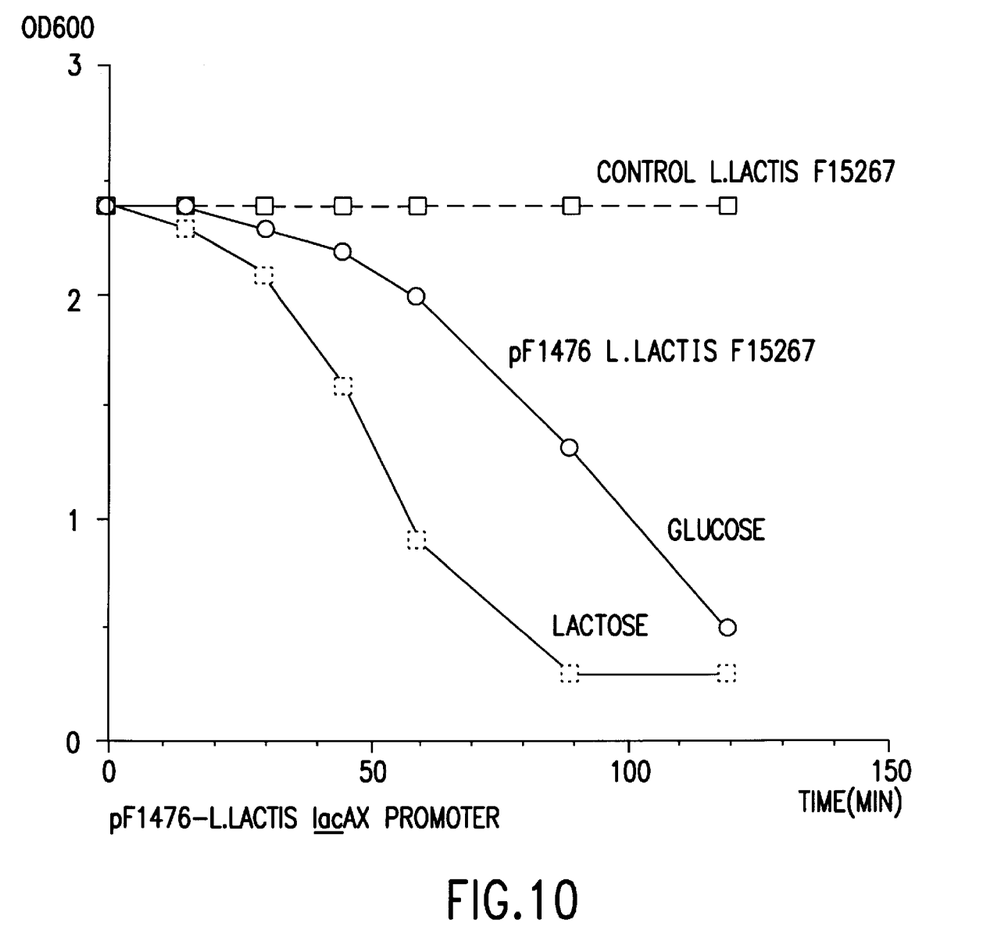
FIG. 10 shows the expression of th e Listeria lysin gene in *Lactococcus lactis* under the control of the lactose inducible lactococcal lactose operon promoter.

The Listeria lysin gene from plasmid pF1328 was isolated together with its own ribosome binding site using the polymerase chain reaction. This fragment was cloned into the PstI site of *E. coli* vector pUC19 in both orientations (plasmids pF1531 and pF1532). Expression of this gene in *E. coli* strains was observed from one orientation only, under the control of the lac α promoter of the vector (plasmid pF1531). Enzyme activity of cell extracts of this strain was comparable to that of *E. coli* strains carrying plasmid pF1322. Using plasmid pF1532 that did not express the lysin gene and cloning the lactococcal lacA promoter/lacR gene on a BamHI fragment (Van Rooijen et al, (1992) *J. Bacteriol.* 174: 2273–2280) upstream of the lysin gene (plasmid pF1533) expression in *E. coli* of φLM-4 lysin from the lactococcal lacA promoter was obtained. The lytic activity of extracts from these *E. coli* strains was lower when the lysin gene was expressed from the lacA promoter. The SstI/SphI fragment of pF1533 containing the φLM-4 lysin gene with the lacA promoter/lacR gene was cloned into the SstI/SphI sites of the lactococcal vector pTG262 (Shearman et al (1989) *Molecular and General Genetics* 218: 214–221) and the resulting plasmid pFI534 was used to transform *L. lactis* MG5267. As shown in FIG. 10 cell extracts of this strain expressed φLM-4 lysin activity when grown on lactose; on glucose enzyme activity of cell extracts was reduced.

The φLM-4 lysin gene together with the lacA promoter/lacR gene was cloned into pF145, a plasmid expressing the *Lactococcus* phage φvML3 lysin gene which causes lysis during stationary phase of *L. lactis* cultures carrying the plasmid (Shearman et al (1992) *Biotechnology* 10: 196–199). The resulting plasmid pFl535 in *L. lactis* MG5267 when grown on lactose produced a culture that grew to stationary phase, then lysed as a consequence of the φvML3 lysin, releasing φLM-4 lysin into the culture supernatant.

EXAMPLE 3

SPECIFIC DETECTION OF MICRO-ORGANISMS

The specificity of a bacteriophage lysin provides an opportunity to specifically detect those micro-organisms which are susceptible to it. For example to detect *Listeria sp.* the lysin described here may conveniently be used at a post enrichment stage where a broth culture of those micro-organisms present in a test sample is first produced. The identity of species of bacteria in the sample at this stage is unknown. The bacterial culture may be centrifuged and resuspended in an assay buffer (eg the one used here in studies of lysin specificity). A control preparation and separately a preparation containing active Listeria lysin are then added. Sufficient units of lysin activity are used to provide very effective lysis of any lysin susceptible cells (i.e. Listeria). After incubation for a short period (eg 30 min) any Listeria present will lyse, but other species will not. The presence of Listeria will then be detected by the lysis of bacteria in the sample treated with the lysin whereas no lysis occurs in the control.

The detection of lysis may be achieved by assaying an intracellular enzyme or metabolite. Especially useful enzyme assays are for phosphatase or for esterase. Alkaline phosphate can be assayed spectrophotometrically by following appearance of p-nitrophenol, which is yellow, from the colourless substrate p-nitrophenyl-phosphate at 405 nm. Esterase activity can be assayed using fluorescein diacetate which is cleaved to acetate and fluorescent fluorescein and measuring the latter in a fluorometer. One especially suitable metabolite assay involves ATP detection. For this the well established luciferase assay in which ATP molecules generate light is exploited. Light emission may be measured in a luminometer. (An example of an end point detection reagent using luciferase-luciferin is marketed by Sigma Chemical Company as product L-1761).

EXAMPLE 4

CLOSTRIDUM TYROBUTYRICUM BACTERIOPHAGE φP1 LYSIN

Bacteriophage φP1 was isolated from a landfill core sample using *Clostridium tyrobutyricum* NCFB 1755 as host. Bacteriophage φP1 was tested against six more strains of *C. tyrobutyricum*. Strains NCFB 1753 and NCFB 1756 supported the growth of bacteriophage and they were thus host strains as was the strain NCFB 1755. Against *C. tyrobutyricum* strains NCFB 1715, NCFB 1754, NCFB 1757 and NCFB 1790 an undiluted φP1 stock suspension gave a clear zone but diluting out did not result in individual bacteriophage plaques. This indicates that these strains were lysin sensitive but not bacteriopnage sensitive. Bacteriophage φP1 thus produces a lysin with a broad specificity for strains of *C. tyrobutyricum*. Similar tests of bacteriophage φP1 with a wide variety of other bacteria showed no effect of the lysin or bacteriophage particles against *C. sporogenes* strains ATCC 17886, NCFB 1789, NCFB 1791; *C. butyricum* strains NCFB 1713, NCFB 857; *Lactobacillus buitineri* strains NCFB 110, F3327; *L. brevis* strains NCFB 1749, F3328; *L. helveticus* strains NCFB 1243, CNRZ 832; *L. bulgaricus* CNRZ448; *L. plantarum* strains NCFB 1752, NCFB 82, NCFB 963; *Escherichia coli* BL 90/12; *Bacillus cereus* NCTC 1143.

Bacteriophage φP1 was deposited at the National Collections of Industrial and Marine Bacteria, 23 St Machar Drive, Aberdeen, AB2 1RY, Scotland on Apr. 5, 1991 and a new deposit was made on Jul. 4, 1991 under the Budapest Treaty and has been accorded accession No NCIMB 40400.

What is claimed is:

1. A method of testing for Listeria bacteria in a sample at the genus level, comprising adding a lytic agent consisting essentially of a bacteriophage lysin substantially free of intact bacteriphage to the sample and determining whether bacterial cells have been lysed thereby; wherein the bacteriophage lysin is derived from bacteriophage of Listerial species.

2. A method as set forth in claim 1 wherein the bacteriophage lysin is derived from the *Listeria monocytogenes* φLM4 culture deposited as NCTC 12453 in the National Collection of Type Cultures.

3. A method as set forth in claim 2 wherein at least some of the bacteria in said sample are unknown.

4. A method as set forth in claim 1 wherein at least some of the bacteria in said sample are unknown.

* * * * *